US005733355A

United States Patent [19]
Hibino et al.

[11] Patent Number: 5,733,355
[45] Date of Patent: Mar. 31, 1998

[54] BACTERIAL PREPARATION FOR AGRICULTURAL USE

[75] Inventors: Susumu Hibino, 7-3-14 Higashi Ohizumi, Nerima-Ku, Tokyo,178; Zenrou Minami, Osaka, both of Japan

[73] Assignees: Susumu Hibino; Nagase Biochemicasl, Ltd.; Risahru Kosan Ltd., all of Tokyo, Japan; a part interest

[21] Appl. No.: 759,448

[22] Filed: Dec. 5, 1996

Related U.S. Application Data

[63] Continuation of Ser. No. 314,667, Sep. 29, 1994, abandoned.
[51] Int. Cl.$^6$ .................................................. C05F 11/08
[52] U.S. Cl. ..................... 71/6; 71/7; 71/903; 435/262; 435/262.5
[58] Field of Search .................... 71/6–8, 903; 435/262, 435/262.5

[56] References Cited

U.S. PATENT DOCUMENTS

| 3,261,688 | 7/1966 | Winfred et al. ........................ 424/115 |
| 4,522,261 | 6/1985 | McInerney et al. ..................... 166/246 |
| 4,861,721 | 8/1989 | Waterbury et al. ................... 435/252.1 |
| 5,147,441 | 9/1992 | Megeed .................................... 71/7 |

FOREIGN PATENT DOCUMENTS

| 3410771 | 5/1985 | Germany. |
| 3918306 | 12/1990 | Germany. |
| 59179037 | 11/1984 | Japan. |
| 379986 | 12/1991 | Japan. |
| 146289 | 6/1993 | Japan. |
| 58832 | 9/1993 | Japan. |

OTHER PUBLICATIONS

Relations between Lipoamino Acids & Soil, Crops, Susumu Hibino, 1991, 19 pages No Month.
Stories of Lipoamino Acids afterwards, Susumu Hibino, 1992 31 pages No Month.
Biosurfactants from Bacillus licheniformis, Katharina Jenny, Othmar Kappeli, Armin Fiechter, May 1991, 9 pages.
Surface–Active Compounds From Microorganisms, George Georgiou, Sung–Chyr Lin and Mukul M. Sharma, Jan. 1992 6 pages.
Isolation and characterization of a surfactant produced by Bacillus licheniformis, Sarah Horowitz, J.N. 6 pages ' 89 No Month.
Anaerobic Production of a Biosurfactant by Bacillus licheniformis JF–2, Mohammad Javaheri, Gary E. Jenneman No date.
Michael J. McInerney, Roy M. Knapp, Jun. 1985, 3 pages.
Isolation of a new peptide antibiotic, permetin A, from Bacillus, Yoshiyuki Takahara, Yoko Takeeuchi, Ichiro Komura Yoshiteru Hirose, Sawao Murao, Aug. 1978 6 pages.
The Structure of Permetin A, A New Polypeptin Type Antibiotic Produced By Baciillus Circulans, Yoko Takeuchi No date.
Asao Murai, Yoshiyuki Takahara and Masatsune Kainosho, Sep. 1989, 10 pages.
Surfactin, A Crystalline Peptidelipid Surfactant Produced by *Bacillus Subtilis*, Kei Arima, Atsushi Kakinuma, Apr. 1968, 7 pages.
Clostridium aerotolerans sp. nov, a Xylanolytic Bacterium from Corn Stove and from the Rumina of Sheep Fed Corn Stover N.O. van Gylswyk, J.J.T.K. van der Toorn, 1987, 4 pages No month.
Clostridium celluloyticum sp. nov., a Cellulolytic, Mesophilic Species from Decayed Grass, E. Petitdemange, F. Caillet, J. Giallo, C. Gaudin, Apr. 1984, 5 pages.
94:439292: BIOSIS Abstract Watanabe et al. Dist & Ident . . . Rice Cultivation, 1993.
92:347678 BIOSIS Abstract, Williams et al. Low Controlled . . . Chrysonthemum. 1992.
85:256955 BIOSIS Abstract, Seldin et al Bacillus Azotofixons . . . Roots, 1984.

*Primary Examiner*—Ferris H. Lander
*Attorney, Agent, or Firm*—Curtis L. Harrington

[57] ABSTRACT

Bacterial preparation which comprises material belonging to genus Bacillus, producing lipopeptides which decrease surface tension of water, and possessing an ability to propagate in soil in the presence of vegetable cellulosic materials under anaerobic condition, and of bacteria belonging to genus Bacillus or genus Clostridium, producing cellulases and possessing an ability to propagate in soil in the presence of vegetable cellulosic materials, and preferably of bacteria belonging to genus Bacillus or genus Clostridium, fixing nitrogen and possessing an ability to propagate in soil in the presence of vegetable cellulosic materials under anaerobic conditions. Examples of lipopeptide-producing bacteria are: *B. subtilis, B. licheniformis, B. circulans*; examples of cellulases-producing bacteria are: *B. subtilis, B. licheniformis, B. circulans, B. polymyxa, B. coagulans, B. macetans, Cl. cellulolyticum, Cl. aerotolerans, Cl. acetobutylicum,* examples of nitrogen-fixing bacteria are: *B. azotofixans, B. macerans, B. polymyxa, Cl. acetobutylicum, Cl. pasturianum.*

3 Claims, No Drawings

BACTERIAL PREPARATION FOR AGRICULTURAL USE

This is a continuation of application Ser. No. 08/314,667 which parent application was filed on Sep. 29, 1994, and now abandoned.

FIELD OF THE INVENTION

The present invention relates to a bacterial preparation used in the fields of plant cultivation and animal husbandry. More specifically, the present invention relates to (1) a bacterial soil conditioner for plant cultivation, (2) a deodorant for feces and urine of animals, and (3) a feed efficiency enhancer for animal feeding.

BACKGROUND OF THE INVENTION

In plant cultivation, many kinds of soil conditioners have been employed to promote productivity. Some of them are microbial preparations, and many of them are aerobic microbial preparations. Though fully fermented compost (compost of high quality) may be produced by employing them, most farmers are reluctant to produce compost even by using these aerobic microbial preparations. There are several reasons for this: first of all, aeration or mixing in special facilities is necessary to employ them in the composting process. Considerable cost for the facilities and much labor is necessary. Also, unpleasant odors are produced in the composting process. In addition, if fully fermented compost is employed in the ordinary farming, several tons of compost per 10a and its continuous use for several years are necessary to attain the desirable result, that is, a condition of soil abundant in humus with adequate degree of formation of aggregates. Thus such soil condition has been attained only by the small portion of farmers called exemplary farmers.

Some anaerobic microbial preparations for plant cultivation and deodorant for feces and urine of animals have been known. However, their effectivity in conditioning soil or deodorizing feces and urine usually lasts for a short period, and their stability in use and preservation is not satisfying enough. It is because they consist mostly of vegetative cells, and most of them are not isolated from soil. Therefore their application is limited, while the frequency and amount of their use cost much. In terms of economy, thus, they are also disadvantaged.

Still some bacterial preparations comprising only one strain of bacteria which belong to genus Bacillus or genus Pseudomomas have once been either marketed or tested in practice as enhancers for fermentating cellulosic materials, soil conditioners, and deodorants for feces and urine of animals. However, all of them have disappeared from the market by now, because one strain of bacteria is not effective enough in different conditions such as their composition, PH, temperature and moisture, in soil, feces and urine and the contents of digestive tracts of animals.

Recently high-yielding varieties have been marketed in many species of crops, and many farmers attempt to attain high levels of yield by using these varieties. Yet they use few compost (or cellulosic materials) but chemical fertilizers too much, with the result that micro-flora in soil changes into an abnormal state, and specific disease-inducing microbes propagate easily. Then as fumigants and antimicrobial agents are used in large amount so as to suppress those microbes, and these components of fertilizers are gradually accumulated in soil, injuries due to continuous cropping is a result. Even now no measures are known to prevent these injuries completely.

Though many deodorants have been marketed to suppress bad odors in barns, their effectivity and economy are unsatisfactory since they are not able to stop completely the process of producing bad odors. Also no products have been known to stop feces and urine from damaging the growth of crops when they are sprinkled over the field instantly after collection from barns. Besides, while some feed-additives as antibiotics have been known to enhance feed efficiency a little, no products have been known to possess the ability both to enhance feed efficiency and to suppress completely bad odors of feces and urine of animals.

SUMMARY OF THE INVENTION

The present invention uses bacterial preparations which comprise material belonging to genus Bacillus, producing lipopeptides which decrease surface tension of water, and possessing an ability to propagate in soil in the presence of vegetable cellulosic materials under anaerobic conditions, and of bacteria belonging to genus Bacillus or genus Clostridium, producing cellulases and possessing an ability to propagate in soil in the presence of vegetable cellulosic materials, and preferably of bacteria belonging to genus Bacillus or genus Clostridium, fixing nitrogen and possessing an ability to propagate in soil in the presence of vegetable cellulosic materials under anaerobic conditions.

Examples of lipopeptide-producing bacteria suitable to the invention are: *B. subtilis, B. licheniformis, B. circulans;* examples of cellulases-producing bacteria are: *B. subtilis, B. licheniformis, B. circulans, B. polymyxa, B. coagulans, B. macerans, Cl. cellulolyticum, Cl. aerotolerans, Cl. acetobutylicum*, examples of nitrogen-fixing bacteria are: *B. azotofixans, B. macerans, B. polymyxa, Cl. acetobutylicum, Cl. pasturianum.* Further details of the invention are extensive and will be described in the detailed description below.

DETAILED DESCRIPTION OF THE PREFERRED EMBODIMENT

The present invention relates to (1) a bacterial preparation for soil conditioning, which comprises bacteria belonging to genus Bacillus, producing lipopeptides which decrease surface tension of water, and possessing an ability to propagate in soil in the presence of vegetable cellulosic materials under anaerobic conditions, and bacteria belonging to genus Bacillus or genus Clostridium, producing cellulases and possessing an ability to propagate in soil in the presence of vegetable cellulosic materials.

The present invention also relates to (2) a bacterial preparation for soil conditioning, which comprises the lipopeptide-producing bacteria, the cellulases-producing bacteria, and bacteria belonging to genus Bacillus or genus Clostridium, fixing nitrogen and possessing an ability to propagate in soil in the presence of vegetable cellulosic materials under anaerobic conditions.

The present invention also relates to (3) a deodorant for feces and urine of animals, which comprises the lipopeptide-producing bacteria and the cellulases-producing bacteria.

The present invention also relates to (4) a feed efficiency enhancer, which comprises the lipopeptide-producing bacteria and the cellulases-producing bacteria.

Lipopeptide, or peptidelipid, normally comprising more than several cyclically-structured amino-acids and a fatty acid combined at an end of their cycle, is a kind of surfactant with hydrophilic and hydrophobic components.

In the present invention, those lipopeptide-producing bacteria which secrete lipopeptides decreasing the minimal surface tension (mN/m) to less than 40 preferably 35 (values by Fisher's Autotensiomat at 25° C.) in its aqueous solution are selectively employed. Typical examples of these lipopeptide-producing bacteria are: *B. subtilis, B. licheniformis, B. circulans*. All of them are spore-forming bacteria.

In the present invention, the term cellulases means enzymes such as cellulase, hemicellulase and pectinase, which are capable of degrading in soil vegetable cellulosic materials such as stems and leaves after crops are harvested, straws, fallen leaves, rice hulls, saw dust, shavings, wooden tips, and bark. Typical examples of these cellulases-producing bacteria are: *B. subtilis, B. licheniformis, B. circulans, B. polymyxa, B. coagulans, B. macerans, Cl. cellulolyticum, Cl. aerotolerans, Cl. acetobutylicum*. All of them are spore-forming bacteria.

The bacteria employed in the present invention are able to propagate in soil in the presence of vegetable cellulosic materials under anaerobic conditions. Since they are isolated from soil and possess the spore-forming ability, the bacteria are very stable in preservation, and able to propagate actively in soil, feces and gut.

Even though one strain of the bacteria possesses both lipopeptide-producing ability and cellulases-producing ability, or both cellulases-producing ability and nitrogen-fixing ability, it is preferable to employ as many different strains as possible for each purpose, so that they will propagate in different conditions in soil, feces and urine, and the contents of digestive tracts of animals, conditions such as their composition, PH, temperature and moisture. More specifically, bacterial preparations in the present invention should be a combination of more than several species or strains for each purpose selected from among lipopeptide-producing bacteria, cellulases-producing bacteria and nitrogen-fixing bacteria.

To degrade or ferment cellulosic materials effectively, their C/N ratio should be within a certain range of figures. If the nitrogen-fixing bacteria in the present invention are used, however, it is not necessary to use nitrogen fertilizers to ferment cellulosic materials, because the bacteria in the present invention are capable of fixing atmospheric nitrogen.

Typical examples of these nitrogen-fixing bacteria are *B. azotofixans, B. macerans, B. polymyxa, Cl. acetobutylicum, Cl. pasteurianum*. All of them are spore-forming bacteria and are not symbiotic with roots of crops.

The lipopeptides employed in the present invention may decrease the surface tension of water drastically in their aqueous solution. In other words, they decrease the viscosity of water and increase the flowability of water, therefore enable water to invade into inner-cells through micro pore-spaces dotted on the surface of living things. When they are secreted in soil, they dissolve in water and enable water to invade through micro pore-spaces dotted on the surface of cellulosic materials. With their invading pressure, they expand the diameters of micro pore-spaces. Consequently, cellulases degrading cell walls and inter-cellular substances, which are normally secreted by other microbs, invade into inner-cells through the expanded pore-spaces. Thus the degradation of not only cell-walls but also inner-cellular substances is promoted.

In addition, when they are secreted in soil, they dissolve in water and enable water to invade through micro pore-spaces dotted on the surface of clay granules. Consequently, they micronize clay granules. Since aggregates consist of a complex of the micronized clay granules and the micronized cellulosic materials degraded by cellulases, it follows that lipopeptides promote the formation of aggregates. They are more stable in soil as compared to lipoamino-acids, which have the similar effect.

Aerobic microbs propagate stably around the outside of aggregates, because there are maintained high levels of air permeability. On the other hand, anaerobic bacteria propagate stably inside aggregates, where there is scarce oxygen because aerobic microbs consume oxygen around the outside of aggregates.

Both lipopeptide-producing bacteria and cellulases-producing bacteria are able to propagate stably in soil where micro aerobic spaces and micro anaerobic spaces are closely situated, and this is the key to maintain symbiotic propagation of each bacterial group.

The secretion of lipopeptides is activated under anaerobic conditions in soil, especially in the early stages of the degradation of cellulosic materials. Yet once cellulosic materials are degraded and softened, few lipopeptides are secreted from fully fermented composts. It is because the secretion is slowed down at the advanced stage of the degrading process. Thus the promoting effect to form aggregates are attained insufficiently if fully fermented compost is used in soil.

It has been common knowledge that compost should not be employed until it is fully fermented, because phenols and volatile nitrogen substances, which are injurious to roots of crops, are produced from unfermented cellulosic materials in the degrading process. However, if farmers employ the present preparation which is selected from bacteria secreting no injurious substances, it is possible not only that the secretion of lipopeptides is activated in the early stages of the degradation of cellulosic materials but also that the preparation of injurious substances from unfermented cellulosic materials is prevented. In other words, when the present preparation is properly used, the formation of aggregates is promoted and the preparation of injurious substances from unfermented cellulosic materials is prevented even in the early stages of the degradation of cellulosic materials.

To prevent injuries by continuous cropping mentioned in the Background of the Invention, and to promote productivity of soil to attain high yield, it is necessary to propagate as many kinds of microbs as possible at high levels in soil so that active propagation of microorganisms inducing specific diseases may be avoided. It requires the conditions where many microorganisms are able to propagate actively, which means promoting the formation of aggregates and maintaining them for a long period in micro spaces where microorganisms are able to propagate.

As lipopeptides are degraded gradually in soil, aggregates are also decomposed. Plowing also promotes the decomposition of aggregates. Thus it is necessary constantly to provide a certain amount of new lipopeptides so that the formation of aggregates may be maintained at higher than a certain level. In other words, it is necessary to use bacterial preparations which may be effective in soil over a long period, and constantly to use a certain amount of unfermented cellulosic materials in soil.

In the present invention, feces and urine is deodorized through the following process. No lipopeptide-producing bacteria have been observed in the digestive tracts of animals as a micro-flora in gut. Although cellulases-producing bacteria are observed in gut, cellulases secreted from the said bacteria cannot act powerfully without lipopeptides: they cannot degrade cell-walls and inter-cellular substances (both of them consist of polysaccharides) of vegetable cells from feed ingredients any further, and most of them are excreted directly to feces in an almost undegraded state. When the bacterial preparation for deodorant in the present invention is sprinkled over feces, lipopeptides are secreted from the bacteria, begins to act on cell-walls and inter-cellular substances which remained in feces, and expand micro pore-spaces dotted on cell walls. At the same time, cellulases which are secreted by co-existing cellulases-producing bacteria begin to degrade cell-walls and inter-cellular substances into smaller components.

So far the following result has been obtained:- indol positive bacteria belonging to genus Clostridium, the main producer of the bad odor substances propagating in large intestine or feces, decrease remarkably ($4 \times 10^5 \rightarrow 3 \times 10^3$/g); on the other hand, indol negative bacteria belonging to genus Clostridium which produce no bad odor substances increase remarkably ($2 \times 10^3 \rightarrow 3 \times 10^5$/g).

Though the similar effect may be attained through sprinkling the lipopeptide-producing bacteria alone, the result is less striking (indol positive bacteria belonging to genus Clostridium: $4 \times 10^5 \rightarrow 2 \times 10^4$/g): it seems that the powerful effect of the lipopeptide-producing bacteria cannot be expected unless they are used along with cellulases-producing bacteria.

The said bacteria of the present invention possess characteristics not to produce volatile nitrogen substances, hydrogen-sulfide or indol, which are the sources of bad odors. Moreover, the bacteria are able to prevent bad odors in barns since the bacteria of the present invention consume the bad odor substances in feces such as ammonia, hydrogen-sulfide, indol, and normal-butyric acid.

This preparation enhance feed efficiency by the following process:- concerning vegetable materials as the main ingredients of domestic animals, substances such as proteins and starches are degraded by several digestive enzymes which invade through the cell-walls, as these substances are packed within the cell-walls. Under the normal condition in which lipopeptide-producing bacteria are not propagating in the gut of animals, the enzymes do not invade through cell-walls or inter-cellular substances efficiently. Accordingly, proteins and starches are insufficiently degraded. However, lipopeptide-producing bacteria enable the several digestive enzymes to invade into the inner-cells through the cell-walls easily, because lipopeptides secreting from the bacteria expand the micro pore-spaces. (Lipopeptide-producing bacteria are not able to propagate permanently in the gut of animals: they propagate as transit bacteria as the result of continuous oral administration.) Therefore, proteins and starches are degraded at first in the cells, and after their molecular weight are minimized enough, the degraded substances easily spin out of the cells through the micro pore-spaces. Then, outside of the cells, the degradation of proteins and starches in feeds are promoted further by the digestive enzymes. This is the process of enhancing digestivity or feed efficiency.

The bacteria of the preparation administered orally also suppress the bad odor substances in the gut of animals by the same process mentioned above. As a result, bad odors of feces smell less strong, which fact helps reduce the physiological stress of animals that inhale them. Accordingly, feed efficiency is enhanced. Though cellulases-producing bacteria originally propagate in the gut of animals, the effect is more remarkable when cellulases-producing bacteria are administered together with lipopeptide-producing bacteria.

Above-mentioned is the description of the processes by which the soil conditioner, the deodorant and the feed efficiency enhancer of the present invention take effect. Though they basically consist of the same bacterial components, the lipopeptide-producing bacteria, coupled with the cellulases-producing bacteria, serve each purpose sufficiently.

In using the soil conditioner of the present invention, cellulosic materials as nutrients to bacteria should be blended into soil as well, and if necessary, an adequate amount of nitrogen sources for fermenting is sprinkled over them. In order to maintain anaerobic conditions, it is necessary to cover them with soil so that their contact with air will be shut out. Usually lipopeptide-producing bacteria begin to propagate on cellulosic materials and nitrogen sources as nutrients in one or two weeks. Cellulases-producing bacteria also begin to propagate simultaneously in their symbiotic relation. Thus the degradation of cellulosic materials and the formation of aggregate are enhanced.

Another method of improving soil conditions by the preparation is to pile cellulosic materials for a short period after mixing the preparation into them, and then use them as compost. This may be applied to less fermentable cellulosic materials such as bark. Also after the preparation is sprinkled over litter in barns, the collected litter is employed to sprinkle over soil. Alternatively, feces and urine of animals to which the preparation is orally administered are employed to sprinkle over soil.

Moreover, the preparation is employed as deodorant by sprinkling over feces and urine in barns, or as feed efficiency enhancer by mixing in animal feeds.

Many barns feeding poultry, swine and cattle employ straws or shavings as litter on the floors. In employing the preparation as deodorant in such barns, an adequate amount of the preparation should be sprinkled over the litter in barn. In two or three weeks lipopeptide-producing bacteria in the preparation begin to propagate actively by consuming undegraded cellulosic materials and nitrogen substances remaining in feces and the litter as nutrients. At the same time, cellulases-producing bacteria in the preparation begin to propagate actively in their symbiotic relation and suppress bacteria producing bad odors in feces and gut.

The life of the bacteria of the preparation tend to be short in feces of animals, because there are no micro pore-spaces for propagating of the bacteria, such as aggregates in soil. Therefore it is more economical to sprinkle the preparation over feces along with porous silicic powders (zeolite, diatomaceous earth, greentuff etc), so that the bacteria will propagate there and their life will be longer, which means the decrease of the amount and frequency of its use.

The main factors determining whether soil are improved on plant cultivated fields are the degree of the formation of aggregate and the amount of minute degraded cellulosic materials such as humus. In the present invention, cation exchange capacity (CEC) and electric conductivity (EC) are adopted as indicators to determine the effects of the preparation, which are most proper and universally used in the fields' work. If aggregates and minute degraded cellulosic materials are sufficiently produced, CEC of cultivated soil increases, because the surface area of these micro granules are expanded as a whole and more components of fertilizers (that is, cations or anions) are absorbed on the surfaces. On the other hand, EC of cultivated soil decrease, because there are less unabsorbed components of fertilizers. However, we should pay attention to the relative values in the same test fields because these values vary according to the cultivated soil.

The feed efficiency means the percentages of the weight of the products of animals against the intakes of feed (measured on dry basis) per fixed weight. It is a indicator on the productivity of meat, egg or milk. The bigger figure means the better feed efficiency.

Bacteria employed in the present invention should be propagated in an appropriate culture medium and under suitable cultivation conditions for each of bacteria in order to form as many spores as possible. If it contains vegetative cells in addition to spores, both are usually dehydrated. Then dried preparations are formulated using appropriate carriers so that the proportion of each of the bacteria may be suitable.

Harvest of spores from the culture in the present invention may be carried out according to a conventional method. The medium used in the present invention may contain any nutritional sources utilizable for each of bacteria of the present invention, such as various carbon, nitrogen, and inorganic metal salts sources.

Especially in the cultivation of the bacteria belonging to genus Bacillus, it is desirable to employ Difco Sporulation Medium of Difco company or its equivalents.

In the cultivation of the bacteria belonging to genus Clostridium, it is desirable to employ medium comprising mineral-salts such as CAMM-*Clostridium acetobutylicum* Sporulation Minimal Medium (as described by Long et al. in 1983, Appl. Environ. Microbiol., 45: 1389–1393) or its equivalents because the sporulation of the bacteria is poor in the nutritionally rich medium.

For the propagation of the bacteria of the present invention, solid culture and agitation culture may be employed. At the completion of the cultivation, any normal separation methods such as centrifugation, filtration and membrane filter separation are applicable to separate the bacteria from the medium, but centrifugation is most desirable when the anaerobic condition is required.

When spores and vegetative cells are to be separated, any conventional methods such as heat treatment, lysozyme treatment and alcohol treatment are applicable to destroy vegetative cells.

As the drying method before the preparation, hot air drying, spray drying and freeze drying are applicable.

The bacterial preparation of the present invention may be prepared by mixing the dried bacterial preparations obtained as mentioned above with suitable carriers. There is no restriction as to the kinds of carriers to be employed; silicic powders such as zeolite, diatomaceous earth and greentuff are applicable.

Although the suitable total number of bacterial preparation in the present invention varies according to bacterial species, but it will be in the range of $10^4$–$10^{10}$ cells/g, preferably $10^5$–$10^8$ cells/g, and the number of spores will be in the range of $10^4$–$10^8$ spores/g, preferably $10^4$–$10^6$ spores/g.

The amount of the bacterial preparation employed in the present invention is not critical and decided suitably according to the objects, conditions, etc. Although the amount of the use as soil conditioner varies according to the contents of cellulosic materials, it will be in the range of 5–40 kg per 10a, preferably 10–20 kg. The amount of the use as deodorant will be in the range of 20–160 g, preferably 40–80 g per 1 square meter for one dosage every 7–8 days. In using as feed efficiency enhancer, it will be blended at the ratio of 0.03–0.3%, preferably 0.05–0.2%, of formula feeds.

The present invention will be described further by the following examples.

EXAMPLE 1

Manufacture of Dried Bacterial Preparation

Bacteria belonging to genus Bacillus, comprising lipopeptides-producing *Bacillus subtilis* ATCC 21332 and *B. licheniformis* ATCC 39307, and cellulases-producing *B. subtilis* ATCC 6051, *B. licheniformis* ATCC 14580, *B. circulans* ATCC 9500 and *B. polymyxa* ATCC 842 etc. were cultivated. Each strain of bacteria was cultivated separately under the following conditions with Difco Sporulation Mediem of Difco company as medium suitable for their sporulation. The cultivation was stopped at an appropriate time between 12 and 48 hours, judging from the progress of cultivation of each strain.

Cultivation Device:
2 L Mini-jar (product of Mitsuwa Rika), 1 L of Medium
Cultivation Condition:

| Air flow | 1L/minute |
| --- | --- |
| Agitation Speed | 400 RPM |
| Temperature | 37° C. |
| Cultivation Time | 12–48 hours |

At the completion of the cultivation, centrifugal separation (10,000 G, 20 minutes) was carried out, and the bacterial cells were collected. The cells were freeze-dried according to the conventional method to produce dried preparations.

The dried preparation was ground in sterile condition, and a certain amount thereof was dispersed into 0.85% physiological saline. Then the total number of bacteria was sought by cultivating them with normal agar (product of Nihon Seiyaku Company) plates as medium. Also after heat treatment at a temperature of 80° C for 15 minutes, the number of the spores was measured by cultivating them similarly.

Anaerobic condition was required for the cultivation of the bacteria belonging to genus Clostridium. In the cultivation of the cellulases-producing bacteria comprising *Clostridium cellulolyticum* ATCC 35319 and *Cl. aerotolerans* ATCC 43524, mineral-salts medium such as CAMM-*Clostridium acetobutylicum* Sporulation Minimal Medium (as described by Long et al.: Appl. Environ. Microbiol., 45: 1389–1393, 1983) was adopted to cultivate separately under the following conditions. The cultivation time was set according to the above condition.

Cultivation Device
2 L Mini-jar (product of Mitsuwa Rika), 1 L of medium
Cultivation Conditions:

| Nitrogen Gas | 0.5L/minute |
| --- | --- |
| Agitation Speed | 200 RPM |
| Temperature | 37° C. |
| Cultivation Time | 12–48 hours |

At the completion of the cultivation, centrifugal separation was carried out under anaerobic conditions in the presence of nitrogen gas to collect bacterial cells. The cells were freeze-dried under anaerobic conditions, and the dried preparation was stored in the presence of nitrogen gas. Then it was ground in sterile conditions, and its total number and the number of the spores were sought with the procedure as mentioned above, except that the plate was replaced with GAM bouillon (product of Nihon Seiyaku) containing 1.5% agar and the cultivation was conducted under anaerobic conditions.

Bacteria belonging to genus Bacillus and genus Clostridium, possessing a nitrogen-fixing ability were cultivated as follows: *Bacillus azotofixans* ATCC 35681 and *B. macerans* ATCC 8244 were cultivated, collected and dried according to the procedure of genus Bacillus as mentioned above; *Clostridium acetobutylicum* ATCC 824, and *Clostridium pasteurianum* ATCC 6013, being required to be cultured under anaerobic conditions, were cultivated, collected and dried according to the cultivation condition of anaerobic bacteria as mentioned above. The total number of the bacteria and the number of the spores of the preparation ground in sterile conditions, were measured according to the procedure of genus Bacillus and genus Clostridium as mentioned above.

EXAMPLE 2

Manufacture of Bacterial Preparation

The dried bacterial preparations obtained in Example 1 was appropriately combined and was mixed with zeolite to obtain the mixed bacterial preparations 1–6 having the desirable number of bacteria.

Table 1 shows the bacterial composition of the six mixed bacterial preparations.

TABLE 1

Compositions of Bacterial Preparations

| No. | Strain Name/ATCC No. | Total No./Cells/g (Spores/g) | Bacterial Prep. 1 | 2 | 3 | 4 | 5 | 6 |
|---|---|---|---|---|---|---|---|---|
| 1 | B. subtilis 21332 | $2.9 \times 10^7 (2.3 \times 10^7)$ | o | o | o | o | o | o |
| 2 | B. licheniformis 39307 | $7.2 \times 10^7 (5.4 \times 10^7)$ | o | o | o | o | o | o |
| 3 | B. subtilis 6051 | $1.4 \times 10^7 (1.3 \times 10^6)$ | o | o | o | o | o | o |
| 4 | B. licheniformis 14580 | $3.6 \times 10^5 (7.2 \times 10^4)$ | o | — | o | o | — | o |
| 5 | B. circulans 9500 | $1.8 \times 10^5 (1.1 \times 10^4)$ | o | — | o | o | — | o |
| 6 | B. polymyxa 842 | $7.6 \times 10^5 (1.2 \times 10^4)$ | — | — | o | o | o | o |
| 7 | Cl. cellulolyticum 35319 | $4.2 \times 10^5 (1.1 \times 10^4)$ | — | o | — | — | o | — |
| 8 | Cl. aerotolerans 43524 | $1.3 \times 10^5 (2.3 \times 10^4)$ | — | o | — | — | o | — |
| 9 | B. azotofixans 35681 | $1.1 \times 10^5 (2.0 \times 10^4)$ | — | — | — | o | — | o |
| 10 | B. macerans 8244 | $1.4 \times 10^5 (2.4 \times 10^4)$ | — | — | — | o | o | — |
| 11 | Cl. acetobutylicum 824 | $2.3 \times 10^5 (1.6 \times 10^4)$ | — | — | — | — | — | o |
| 12 | Cl. pasteurianum 6013 | $4.2 \times 10^5 (1.0 \times 10^4)$ | — | — | — | — | o | — |

The present invention will be described further by the following applications.

Application 1: Example of Soil Conditioner

| Crops | Wheat |
|---|---|
| Variety | Norin 61 |
| Cultivated Term: | |
| Sowing | end of October |
| Harvest | middle of the next June (in Gunma Prefecture) |
| Cellulosic Material Rice Straws: | |
| Test Lot | 530 |
| Marketed Preparation Lot | 530 (kg/10a) |
| Urea for Fermentation | |
| Test Lot | 5 |
| Marketed Preparation Lot | 4 (kg/10a) |
| Bacterial Preparations Kind: | |
| Test Lot | Bacterial Preparation 1 of Example 2 |
| Marketed Preparation Lot | Super Karuson NR-C (anaerobic bacterial preparation for soil conditioner, by Chiba-Bio Kosan LTD, number of total bacteria: $3 \times 10^8$/g) |
| Quantity: | |
| Test Lot | 10 |
| Marketed Preparation Lot | 20 (kg/10a) |

A control lot using no bacterial preparation was added.

The amount of chemical fertilizers of N,P,K is equal on three lots (the amount of chemical fertilizers is equal in the tests of plant cultivation as mentioned below unless otherwise noticed).

Use of Preparations:

The preparation and urea were evenly sprinkled after straws harvested in the same year had been sprinkled over the fields, and covered with soil 10–15 cm deep. Sowed a day after its use. No straws were used on the control lot.

Summary of Results:

| Yields: | |
|---|---|
| Test Lot | 405 |
| Marketed Preparation Lot | 382 |
| Control Lot | 345 (kg/10a) |
| Thousand kernel Weight: | |
| Test Lot | 37.5 |
| Marketed Preparation Lot | 36.8 |
| Control Lot | 36.1 (g) |

Indicator: (the values in early June, measured on soil sampled 15 cm under the ground. Same as until Application 7)

| CEC: | |
|---|---|
| Test Lot | 13.6 |
| Marketed Preparation Lot | 11.2 |
| Control Lot | 8.9 (me/100 g) |
| EC: | |
| Test Lot | 0.2 |
| Marketed Preparation Lot | 0.3 |
| Control Lot | 0.7 (ms/cm [1:5]) |

Description:

Neither of the wheat on the test lot nor of the marketed preparation lot were injured by frost in early spring, because on both of the lots the roots spreaded vigorously and the stems growed late enough. After May the wheat growed well on both of the lots. Though the amount of the bacterial preparation on the marketed preparation lot was sprinkled twice as large as that on the test lot, the yield of the marketed preparation lot was a little lower than that of the test lot. On the other hand, on the control lot the roots spreaded weakly and the stems growed too early. Therefore they were injured by frost, and the growth was retarded and the yield decreased.

Analysis:

The degree of soil improvement may be determined by the values of CEC and EC of each lot measured just before the harvest. Though the bacteria of the preparation passed winter, sufficient soil improvement was attained especially on the test lot, because the bacteria was able to propagate actively from spring to early summer in the test lot. That shows the yield of the wheat and the thousand kernel weight.

Application 2: Example of Soil Conditioner

| Crops | Rice Plant |
|---|---|
| Variety | Kinuhikari |
| Cultivated Term: | |
| Replant | early June |
| Harvest | end of October |
| | (in Nagano Prefecture) |
| Cellulosic Materials | |
| Rice Straws: | |
| Test Lot | 300 |
| Marketed Preparation Lot | 300 (kg/10a) |
| Rice Hulls: | |
| Test Lot | 200 |
| Marketed Preparation Lot | 200 (kg/10a) |
| Urea for Fermentation | |
| Test Lot | 5 |
| Marketed Preparation Lot | 4 (kg/10a) |
| Bacterial Preparations | |
| Kind: | |
| Test Lot | Bacterial Preparation 2 of Example 2 |
| Marketed Preparation Lot | the same preparation used in Application 1 |
| Quantity: | |
| Test Lot | 10 |
| Marketed Preparation Lot | 10 (kg/10a) |

A control lot using no bacterial preparation was added.
Use of Preparations:
Cellulosic materials were evenly sprinkled over the paddy fields 3 days before replanting at puddling and leveling in both the test lot and marketed preparation lot as well as urea and the bacterial preparations. They were covered with soil 10–15 cm deep. No cellulosic materials were used on the control lot.
Summary of Results:

| Effective Tillers per one Hill: | |
|---|---|
| Test Lot | 29.3 |
| Marketed Preparation Lot | 26.7 |
| Control Lot | 22.3 |
| Yields of Brown Rice: | |
| Test Lot | 684 |
| Marketed Preparation Lot | 648 |
| Control Lot | 633 (kg/10a) |
| Thousand kernel Weight of Brown Rice: | |
| Test Lot | 20.8 |
| Marketed Preparation Lot | 20.6 |
| Control Lot | 20.6 (g) |
| Indicator | (the values in early August) |
| CEC: | |
| Test Lot | 31.6 |
| Marketed Preparation Lot | 26.4 |
| Control Lot | 23.6 (me/100 g) |
| EC: | |
| Test Lot | 0.05 |
| Marketed Preparation Lot | 0.2 |
| Control Lot | 0.6 (ms/cm [1:5]) |

Description:
It is common knowledge that, if cellulosic materials are sprinkled into paddy fields in replanting just before early summer as in this case, bubbling (phenomenon that roots and plant are damaged through secreting hydrogen-sulfide or methane as the result of anaerobic fermentation in paddy fields when water temperature raise suddenly at early summer) is often observed. In this case, though cellulosic materials were used 3 days before replanting, no sign of bubbling was observed in the test lot.

This is because lipopeptides and cellulases were actively secreted from the bacterial preparation, cellulosic materials were degraded in a very short period, and no components injurious to roots were produced in degrading the cellulosic materials.

While on the other hand, bubbling was observed in the marketed preparation lot in early summer. This is because cellulosic materials were degraded so slowly because of its weak degrading ability, and the components injurious to roots were produced in degrading the cellulosic materials. As a result, the growth retarded, the tillers were fewer than that in the test lot, and the yield decreased considerably.

Analysis:
Soil was sampled on each lot 15 cm under the ground in early August, after 2 months from the beginning of the test. 100 g of the sample from each lot and 400 ml of water were poured into a beaker and mixed sufficiently, and the mixture was poured into graduated cylinders of 5×30 cm. Though larger granules of soil precipitated immediately, very fine granules were floating in the upper phase. The time at which the upper 6 cm was clarified was measured respectively: 4.5 hrs for the control lot; 18 hrs for the marketed preparation lot; more than 30 hrs for the test lot. This shows aggregates consisting of very fine clay granules were formed on the test lot most remarkably.

The values of CEC and EC support this conclusion. Though the values of CEC on the other lots were relatively high because of abundant clay in original paddy fields, the value on the test lot is higher than those because the formation of aggregates was especially promoted.

Application 3: Example of Soil Conditioner (A case of Used after Composting)

| Crops | Melon |
|---|---|
| Variety | Andes |
| Bacterial Preparations: | |
| Test Lot | bacterial preparation 3 of Example 2 |
| Marketed Preparation Lot | the same as Application 1 |

A control lot using no bacterial preparation was added.
Test Term:

| Beginning of Composting: | |
|---|---|
| Test Lot | early March |
| Marketed Preparation Lot | late February |
| Control Lot | early September of the previous year |

-continued

| Cultivation | |
|---|---|
| All lots | from early March (in Saitama Prefecture) |

Use of Preparations:

4 tons of composts consisting mainly of inedible parts of vegetables and fruits, and partly of fishes and meats, supplied by the concentrated kitchen of a restaurant chain, were collected per lot (30–35 on C/N ratio, 75–80% of moisture). 2 kg and 4 kg of each bacterial preparation were sufficiently mixed with 40 kg of porous zeolite powders (3–30 μm of the diameters of pores), respectively. Then each of the mixed powders was mixed well with 4 tons of the above composts, and were piled conically covered with plastic sheets to shut out air. After that they were left for 4 or 8 days, respectively. The compost for the control lot was left as it was, stirred well totally every 2 weeks for high air permeability, and piled for 6 months. At the ratio of 4 t/10 a, each of the composts produced as mentioned above was directly sprinkled over the fields in non-heated plastic greenhouse, and covered with soil 10–15 cm deep. Then seedlings of melon were planted.

Summary of Results:

Plant on each lot growed well and adjustment was made so that 3 melons per each hill may grow.

Average weight of melon at harvest time in the middle of June:

| Test Lot | 920 |
|---|---|
| Marketed Preparation Lot | 908 |
| Control Lot | 842 (g) |
| Contents of sugar: | |
| Test Lot | 14.8 |
| Marketed Preparation Lot | 14.4 |
| Control Lot | 13.4 (%) |

Though the composts were piled for as short as 4 days on the test lot and 8 days on the marketed preparation lot, the plants suffered no injury in growing, because raw composts were fermented speedily in soil, and no injurious substances were produced at the early stage of fermentation when these bacterial preparations were employed.

Indicator: (the values in early June)

| CEC: | |
|---|---|
| Test Lot | 10.5 |
| Marketed Preparation Lot | 9.1 |
| Control Lot | 6.8 (me/100 g) |
| EC: | |
| Test Lot | 1.8 |
| Marketed Preparation Lot | 2.2 |
| Control Lot | 3.2 (ms/cm [1:5]) |

Description:

Though the amount of the bacterial preparation used on the test lot was only 50% as large as on the marketed preparation lot, the piling period was shorter, and the temperature was relatively low in the former half of the test period, a very advantageous result was gained on the test lot, because the bacteria possessed a high affinity to soil and a spore-forming ability and propagated stably and actively even on low temperature.

Analysis:

The degree of soil conditioning could be measured on each lot with the values of CEC and EC just before harvesting. Because an accumulation of salts was advanced as the result of cultivation in greenhouse for several years, the values of EC on the other lots were relatively high. Nevertheless the value on the test lot is considerably low. The values of CEC and EC are reflected in the yields of melons and the content of sugar on each lot.

Application 4: Example of Soil Conditioner

| Crops | burdock |
|---|---|
| Variety | Mitoyo-Shirohada |
| Cultivated Term: | |
| Sowing | middle of October (3 days after organic fertilizers were used) |
| Harvest | end of next June (in Chiba Prefecture) |
| Cellulosic Materials Rice Straws: | |
| Test Lot | 300 |
| Marketed Preparation Lot | 300 (kg/10a) |
| Rice Hulls: | |
| Test Lot | 350 |
| Marketed Preparation Lot | 350 (kg/10a) |
| Urea for Fermentation | |
| Test Lot | 0 |
| Marketed Preparation Lot | 4 (kg/10a) |
| A control lot was added. | |
| Burdocks were cultivated on sandy soil (aggregate were not apt to form for little clay soil). | |
| Bacterial Preparations: | |
| Kind: | |
| Test Lot | Bacterial Preparation 4 of Example 2 |
| Marketed Preparation Lot | the same preparation used in Application 1 |
| Quantity: | |
| Test Lot | 10 |
| Marketed Preparation Lot | 20 (kg/10a) |

Use of Preparations:

10 kg of the bacterial preparation of the test lot was mixed well with about 50 kg of a mixture of the almost same amount of rapeseed oil meal, crude fish meal, bone meal, rice bran and soy bean oil meal, and 100 g of porous greentuff powders (whose diameter is 3–30μ long). To adjust the moisture of the mixture to 55%, the mixture was covered by plastic sheets. The test lot was left as it was in the room temperature. Given this treatment, a group of bacteria came to propagate in the micro pore-space of porous greentuff powders.

On the marketed preparation lot the same treatment was made except that the amount of the bacterial preparation was twice as large as on the test preparation, and it was left for 20 days. On the control lot, the same organic fertilizers were piled for 3 months and sometimes mixed meanwhile.

In this test no chemical fertilizers were employed. Cellulosic materials and organic fertilizers produced as mentioned above were sprinkled over soil and covered with soil 15 cm deep. No cellulosic materials were used on the control lot.

Summary of Results:

Marketable Yields:

| | |
|---|---|
| Test Lot | 2.46 |
| Marketed Preparation Lot | 2.34 |
| Control Lot | 2.15 (t/10a) |
| Indicator | (the values in early June) |

CEC:

| | |
|---|---|
| Test Lot | 6.4 |
| Marketed Preparation Lot | 5.2 |
| Control Lot | 3.6 (me/100 g) |

EC:

| | |
|---|---|
| Test Lot | 0.06 |
| Marketed Preparation Lot | 0.2 |
| Control Lot | 0.4 (ms/cm [1:5]) |

Description:

A part of groups of bacteria died on the marketed preparation lot, because the cultivating term was so long that the burdocks passed winter, and the marketed preparation was not stable enough in its sandy soil. Therefore the result on the marketed preparation lot was a little inferior to that on the test lot, notwithstanding the fact that double the amount of the preparation was employed on the marketed preparation lot.

Analysis:

The degree of soil conditioning could be measured on each lot with the values of CEC and EC just before the harvest time. Though the values of CEC on the other lots were relatively low because of the sandy soil, the value on the test lot is higher than those. The yields of the burdocks support the values.

Application 5: Example of Soil Conditioner

| | |
|---|---|
| Crops | Rice Plant |
| Variety | Hananomai |
| Cultivated Term: | |
| Replant | early May |
| Harvest | middle of October |
| | (in Yamagata Prefecture) |
| Cellulosic Material | |
| Rice Straws: | |
| Test Lot | 580 |
| Marketed Preparation Lot | 580 (kg/10a) |
| Urea for Fermentation | |
| Test Lot | 0 |
| Marketed Preparation Lot | 4 (kg/10a) |
| A control lot was added. | |
| Bacterial Preparations: | |
| Kind: | |
| Test Lot | Bacterial Preparation 5 of Example 2 |
| Marketed Preparation Lot | the same preparation used in Application 1 |
| Quantity: | |
| Test Lot | 10 |
| M.P. Lot #1 | 10 (used on April) |
| M.P. Lot #2 | 20 (used on December) (kg/10a) |

Use of Preparations:

The bacterial preparation of the test lot was sprinkled in December over the rice straws which were left on the fields after harvesting the paddy, and they were left as they were (through the first snowfall in the middle of December, the accumulation of snow by the end of December, and the thawing in the middle of March) until early April, when the bacterial preparation was blended into soil with the straws, and covered with soil 10–15 cm deep at puddling and leveling.

Almost at the same time, the preparation was used on the marketed preparation lot #2. In addition, 4 kg of urea was used at puddling and leveling on this lot.

On the marketed preparation lot #1 the preparation and urea were simultaneously blended into soil at puddling and leveling. No straws were used on the control lot.

Summary of Results:

Yields of Brown Rice:

| | |
|---|---|
| Test Lot | 620 |
| M.P. Lot #1 | 612 |
| M.P. Lot #2 | 615 |
| Control Lot | 583 (kg/10a) |

Effective Tillers per Hill

| | |
|---|---|
| Test Lot | 22.5 |
| M.P. Lot #1 | 22.2 |
| M.P. Lot #2 | 22.4 |
| Control Lot | 21.0 |

Thousand Kernel Weight of Brown Rice

| | |
|---|---|
| Test Lot | 22.5 |
| M.P. Lot #1 | 22.2 |
| M.P. Lot #2 | 22.3 |
| Control Lot | 21.3 (g) |
| Indicator | (the values in early July) |

CEC:

| | |
|---|---|
| Test Lot | 30.2 |
| M.P. Lot #2 | 28.1 |
| Control Lot | 23.1 (me/100 g) |

EC:

| | |
|---|---|
| Test Lot | 0.2 |
| M.P. Lot #2 | 0.3 |
| Control Lot | 0.5 (ms/cm [1:5]) |

Description:

On the marketed preparation lot #2 part of groups of the bacteria died, because they consisted mainly of vegetative cells and were exposed directly to air in winter. Therefore the effect had not been so remarkable on the marketed preparation lot #2, even though the preparation was blended at the ratio of 20 kg/10 a in December.

By contrast, few groups of the bacteria died on the test lot while passing winter, and the result exceeded not just the one on the marketed preparation lot #2, but the one on the marketed preparation lot #1, where the preparation was sprinkled in April. It means that the present preparation is also advantageous in terms of effective labor distribution because it may be used in December, the slack season for farmers. Still, unlike on the marketed preparation lots, it was not necessary to use urea on the test lot, because nitrogen-fixing bacteria were contained in the preparation.

Analysis:

The clarification test of soil was not executed this time. Instead, when the inventor walked on the paddy field in bare feet, it was confirmed that on the test lot the field was felt by soles soft and smooth, on the marketed preparation lot #2 it felt rather hard and rough, and on the control lot it felt hard and rough. The feelings as well as the values of CEC or EC showed that aggregates formed most remarkably on the test lot.

Application 6: Example of Soil Conditioner (A Case of Using Compost of Bark)

| Crops | Tomato |
|---|---|
| Variety | Momotaro |
| Test Term: | |
| Beginning of Composting | |
| Test Lot | early December |
| Marketed Preparation Lot | early November |
| Control Lot | early September of the previous year |
| Beginning of Cultivation: | |
| All Lots | middle of February (in Shizuoka Prefecture) |
| Bacterial Preparations: | |
| Kind: | |
| Test Lot | Bacterial Preparation 6 of Example 2 |
| Marketed Preparation Lot | the same preparation used in Application 1 |

Use of Preparations:

10 tons of barks of broad-leaved trees and coniferous trees (partly including timber tips), collected from pulp factories and sawmills, were ground to pieces several centimeter long. In order to adjust C/N ratio and make fermentation easy, 2 tons of feces of chickens, 1 ton of shell fossil powders, 1 ton of rice bran and 1 ton of okara, by-product of the tofu (soybean-curd) preparation process, were mixed with them, and adjusted so that they contained 75% of moisture.

After that (1) 10 kg of the preparation and (2) 20 kg of the preparation were respectively added to the bark mixture produced in an above-mentioned way. For control lot, (3) the simple bark mixture was prepared. (1) was covered with plastic covers and piled for 3 months on the concrete floor. (2) was covered with plastic covers and piled for 4 months on the concrete floor. (3) was aerated from the bottom by the air pump every month and piled for 18 months.

3 t/10a of each of these composts of barks was blended into the fields over the greenhouse, where the heating system worked in winter (from the middle of November to early March), and covered with soil 10–15 cm deep. Then seedlings of tomatoes were planted.

Summary of Results:

The harvest had started in April. On the test lot collecting tomatoes at the 11th nods (in late November) was still profitable enough. On the marketed preparation lot collecting tomatoes at the 10th nods (in early November) was profitable, and on the control lot collecting tomatoes at the 8th nods (in early September) was so. Tomatoes were cultivated continuously every year on each lot in the same cropping type as mentioned above and by blending each compost of barks.

Even after 7 years had passed, the yield on the test lot did not decrease. On the marketed preparation lot the yield in the 6th year decreased by 12% as compared to the average until the previous year. On the control lot the yield had already decreased by 22% in the 5th year, therefore other crops were planted instead of tomatoes after the year.

Indicator: (the values in the middle of May in the 5th year)

| CEC: | |
|---|---|
| Test Lot | 8.7 |
| Marketed Preparation Lot | 7.1 |
| Control Lot | 3.7 (me/100 g) |
| EC: | |
| Test Lot | 0.8 |
| Marketed Preparation Lot | 1.8 |
| Control Lot | 3.4 (ms/cm [1:5]) |
| (the values in the middle of May in the 6th year) | |
| CEC: | |
| Test Lot | 8.4 |
| Marketed Product Lot | 6.4 (me/100 g) |
| EC: | |
| Test Lot | 0.9 |
| Marketed Preparation Lot | 2.0 (ms/cm [1:5]) |

Description:

Crops belonging to Solanaceae, such as tomatoes, are considered to be so easily injured by continuous cropping that it is difficult to cultivate them on the same fields for more than 5 consecutive years even though a large amount of composts is blended into soil year by year. Yet if the bacterial preparation is adequately used as seen on the test lot, it is possible to cultivate them continuously over long periods on the same fields without changing the soil in the greenhouse, which saves a lot of trouble. In addition, though the amount of the use of the preparation employed on the test lot was half as large as that employed on the marketed preparation lot, and the piling term of composts of barks was only 3 months in winter, no injuries of crops were observed on the test lot, because injurious substances were not produced in the fermentation process after cellulosic materials were blended into soil. This is very advantageous for both producers of composts of barks and farmers.

Analysis:

The values of CEC and EC in the 5th year of continuous cropping on the control lot showed that tomato cultivation would be difficult any more there, because soil was insufficiently conditioned. Whereas the values of CEC and EC on the test lot showed that the soil were sound enough still in the 6th year, in spite of 6 years of continuous cropping. This enables continuous cropping over such a long period.

Application 7: Example of Soil Conditioner (A Case of Permanent Crops)

| Crops | Pears |
|---|---|
| Variety | Kosui |
| Cultivating Term | (Permanent) |
| Test Lot | 20 stands of pentanial plants |
| Marketed Preparation Lot | 20 stands of pentanial plants |
| Control Lot | 20 stands of pentanial plants (in Ibaragi Prefecture) |
| Bacterial Preparations: | |
| Kind: | |
| Test Lot | Bacteral Preparation 4 of Example 2 |
| Marketed Preparation Lot | the same preparation used in Application 1 |
| Quantity: | |
| Test Lot | 150 |
| Marketed Preparation Lot | 150 (g per hole) |
| Times: | |
| Test Lot | Once |
| Marketed Preparation Lot | Twice (per year) |
| Total Amount in One Year | |
| Test Lot | 600 |
| Marketed Preparation Lot | 1200 (g per plant) |

Cellulosic Material etc:

At four points of 2–2.5 m apart from the plants, four holes of 60×70 cm were digged like as many octopus catching pots.

On the test lot 6 kg of trimmed twigs cut to pieces 10–15 cm long, 6 kg of cattle feces which contained sawdust as litters just after collected from barn and 70 g of LP nitrogen fertilizer were put in per hole. On the marketed preparation lot 100 g of urea put in per hole.

Use of Preparations:

On the test lot the preparation was scattered over into the holes in which the cellulosic materials had been put in, mixed well, pressed sufficiently, and covered with soil 15 cm deep at the end of November. On the marketed preparation lot, the preparation was scattered over into the holes in the same way (except that the cellulosic materials were rice hulls instead of twigs) both in the middle of September and in the middle of March. On the control lot no cellulosic materials were employed.

In the 2nd year on the test lot and on the marketed preparation lot new holes were digged near the first holes and the same treatment was made.

Summary of Results:

| Marketable Yields of the 2nd Year per 20 Stands: | |
|---|---|
| Test Lot | 2.34 |
| Marketed Preparation Lot | 2.24 |
| Control Lot | 2.04 (t) |
| Average Weight: | |
| Test Lot | 293 |
| Marketed Preparation Lot | 288 |
| Control Lot | 274 (g) |
| Contents of Sugar: | |
| Test Lot | 13.2 |
| Marketed Preparation Lot | 13.0 |
| Control Lot | 12.3 (%) |

Indicator: (the values in July in the second year near the holes)

| CEC: | |
|---|---|
| Test Lot | 9.2 |
| Marketed Preparation Lot | 8.2 |
| Control Lot | 5.8 (me/100 g) |
| EC: | |
| Test Lot | 0.3 |
| Marketed Preparation Lot | 0.4 |
| Control Lot | 0.8 (ms/cm [1:5]) |

Description:

The result on the test lot, where the preparation was administered once a year, exceeded the result on the marketed preparation lot, where the preparation was administered twice a year. In addition, it meant that on the test lot it was possible to attain a good result by putting to use cellulosic materials hard to degrade such as twigs, whereas it would have been very difficult to use them on the marketed preparation lot. This was because the bacteria on the test lot produced lipopeptides and cellulases so vigorously that twigs were degraded sufficiently.

Analysis:

Because fruits trees are permanent and usually have large roots spread, it takes a relatively long time to improve the soil around them. However, the values of CEC and EC in the second year demonstrated that the soil was conditioned considerably on the test lot. The yields as well as the contents of sugar of pears support these values.

Application 8: Example of Deodorant (A Case of Feces Deodorization and Dedamaging of Drainage from Cattle Barns)

| Objects: | Dairy Cattle (Holstein) |
|---|---|
| Perennial Pasture | (Clover and Orchard-grass) |
| Test Term | May–April in the next year (in Obihiro, Hokkaido) |
| Litters: | |
| All Lots | Rice Straws |
| Bacterial Preparations: | |
| Test Lot | Preparation 2 of Example 2 |
| Marketed Preparation Lot | Risaru C-20 (Anaerobic Bacterial Preparation for Deodorant by Bio-Risaru Research Institute LTD, number of total bacteria: $3 \times 10^8$/g) |

Use of Preparations:

The test and marketed bacterial preparations were fully mixed with their 9 times weight of porous powders of zeolite (whose diameter was 3–30 pm long) and sprinkled over litters. On the test lot 400 g of the preparation processed in an above-mentioned way were sprinkled over the floor of the barns every 8 days per 1 square meter. On the marketed preparation lot 400 g of preparation processed as above mentioned were sprinkled over the floor of the barns every 4 days per 1 square meter.

Summary of Results:

The experiment started in May. Bad odors in the cattle barns almost disappeared in 2 weeks on both of the lots. On the test lot no flies were seen in the cattle barns 10 days after the beginning of use: on the marketed preparation lot 2 weeks after the beginning of use.

Contents of Ammonia and Normal-butyric Acid (Measured 20 days after the beginning of the use, one meter high from the ground at the middle of the cattle barns)

| | Ammonia | Normal-butyric Acid |
|---|---|---|
| Test Lot | 2.5 | 0.001 |
| Marketed Preparation Lot | 3.5 | 0.003 |
| Control Lot | 17.0 | 0.03 (ppm) |

The values of the test lot and the marketed preparation lot were the average of three points. The values of the control lot were the average of two points. Considerable bad odors were smelled on the control lot.

Less than 5 ppm of ammonia were not smelled.

| Average Milk Gains per Cattle per Year: | |
|---|---|
| Test Lot | 390 kg (the average of 92 head of cattle) |
| Marketed Preparation Lot | 382 kg (the average of 87 head of cattle) |
| Control Lot | 0 kg (the average of 85 head of cattle) |

(5.4% more on test lot, 4.6% more on marketed preparation lot compared to control lot)

In 3 months, on the test lot, straws floating on the upper parts of the drain pits softened completely and the drainage was therefore easily pumped up from the cattle barns by vacuumed hoses. On the marketed preparation lot it was a little difficult to pump up the drainage from December to March. On the control lot it was very difficult.

Even when the drainage from the test lot was directly sprinkled over the pasture, no bad influence over the growth of the pasture was observed. On the drainage from the marketed preparation lot no bad influence over the growth of the pasture was observed, either. On the other hand, the drainage from the control lot, when directly sprinkled over the pasture, caused part of the pasture to blown. As a result, their growth was retarded, and it took 4 months to recover the normal growth tempo. Later it was proved that the drainage should be left for at least three months so that sprinkling would provide no injuries.

On the marketed preparation lot, bad odors of hydrogen-sulfide (0.01 ppm) was smelled in the drain pits from the middle of December to early March. On the test lot, no bad odors was smelled or detected even in the same term. On the control lot strong bad odors was smelled especially in summer.

Description:

The equal or better effects were observed on the test lot in spite of half the times of the use of the test preparation as compared to that of the marketed preparation. It ascribed to the difference in the propagating ability between the bacteria of the preparations. In terms of preventing the nuisance of animal husbandry it was noticeable that in a certain time no flies were observed both on the test lot and on the marketed preparation lot.

Analysis:

On the marketed preparation lot, straws were not sufficiently softened in the pits and hydrogen-sulfide was produced, because the activity of the bacteria of the marketed preparation was restricted in winter. Whereas no such phenomena were observed on the test lot.

The decrease in bad odors in the cattle barns led to the decrease in the physiological stress of cattle, which resulted in the increase in the average milk gain on the test lot.

Application 9: Example of Deodorant (A Case of Feces Deodorization and Dedamaging of Composts from Chicken Feces)

Objects: Layer (Hyline) Cabbage (Nakawase No.2)

Test Term: October-March in the next year

Seedlings of cabbages were planted in the middle of November and harvested at the end of next May (in Saitama Prefecture)

| Litters: | |
| --- | --- |
| Test Lot | Shavings |
| Marketed Preparation Lot | Shavings |
| Control Lot | Straws |
| Bacterial Preparations: | |
| Test Lot | The same processed preparation as in the application 8 |
| Marketed Preparation Lot | The same processed preparation as in the application 8 |

Use of Preparations:

On each lot 1000 birds of chickens were fed on the floor in windowless barns. Both on the test lot and on the marketed preparation lot 500 g per one square meter of each of the processed preparations had been sprinkled over the floor every 8 days since the middle of October. 1 month after the sprinkling, chicken feces including shavings were collected and immediately blended into the fields at the ratio of 2 t/10a. They were covered with soil 10–15 cm deep. 4 days after this seedlings of cabbages were planted.

On the control lot chicken feces including the litters were piled conically on the concrete floor, and left for 2 months with occasional mixing. After they were almost fermented, they were blended into soil at the ratio of 3 t/10a.

Summary of Results:

Contents of Ammonia and Normal-butyric Acid (Measured 2 weeks after the sprinkling one meter high from the ground at the middle of the chicken barns)

| | Ammonia | Normal-butyric Acid |
| --- | --- | --- |
| Test Lot | 2.0 | Not Detected |
| Marketed Preparation Lot | 4.3 | 0.0007 |
| Control Lot | 7.5 | 0.03 (ppm) |

On the test lot and on the marketed preparation lot no bad odors were smelled, while on the control lot they were smelled.

| Average Egg Laying Rate: | |
| --- | --- |
| (The values of laying-hens 7–12 months old for the 6 months from the middle of November to the middle of next May) | |
| Test Lot | 85.2 |
| Marketed Preparation Lot | 84.9 |
| Control Lot | 83.9 (%) |
| Average Weight of an Egg: | |
| Test Lot | 65.2 |
| Marketed Preparation Lot | 64.1 |
| Control Lot | 63.3 (g) |
| Marketable Yields of Cabbages: | |
| Test Lot | 5.84 |
| Marketed Preparation Lot | 5.61 |
| Control Lot | 5.12 (t/10a) |
| Average Weight of Cabbages: | |
| Test Lot | 1.54 |
| Marketed Preparation Lot | 1.48 |
| Control Lot | 1.35 (kg) |

Description:

The equal or better effects were observed on the test lot in spite of half the times of the use of the test preparation as compared to that of the marketed preparation. It ascribed to the difference in the propagating ability between the bacteria of the preparations.

Analysis:

The total average weight of eggs (the laying rate×the average weight of an egg) on the test lot exceeded by 4.6% that on the control lot. It is because the chickens on the control lot suffered much more physiological stress from bad odor substances such as ammonia which were produced from the chickens' feces and confined in the windowless barns.

Application 10: Example of Enhancing Feed Efficiency

| Animals | Beef Cattle |
| --- | --- |
| Variety | Castrated Holsteins |
| Bacterial Preparation: | |
| Test Lot | The same processed preparation as in |

-continued

| Test Term | the application 8<br>A control lot was added.<br>the end of December–the end of March in the next year (in Wakayama Prefecture) |

Use of Preparation:

1 ton of the skins of oranges and other by-products produced in orange juice factories (moisture 75%) were mixed with 3 kg of the preparation and added 0.7% of di-ammoniummono-hydrogen phosphate on the concrete floor. They were covered with plastic covers, left as they were for 3 days.

Then formula feeds for beef cattle and the orange skins above mentioned were mixed at the ratio of 70% to 30% by the apparent weight. The mixed formula feeds as well as rice straws were fed to 10 head of cattle (whose average weight is 450 kg) on free choice. The orange skins on the control lot were processed nearly the same way, and piled and left for 6 days.

Summary of Results:

The body weight of each cattle was measured every 30 days from the beginning of the test.

| Weight Gains for 3 Months per Day per Head: | |
|---|---|
| Test Lot | 1.12 |
| Control Lot | 1.03 (kg) |

Bad odors of feces excreted disappeared 2 weeks after the beginning of the test. Bad odors from feces in the total barns disappeared 1 month after (content of ammonia:4 ppm). Bad odors from feces excreted persisted on the control lot (content of ammonia:14–18 ppm).

Feed Efficiency:

(The values for the last 3 months: the weight of feed was measured on dry basis.)

| test lot | 15.6 |
|---|---|
| control lot | 14.3 (%) |

Description:

The bad odors on the test lot disappeared, because the spore-forming bacteria propagated vigorously while passing through the gut (especially the large intestine) of the cattle.

Analysis:

The feed efficiency on the test lot exceeded the one on the control lot by 9.0%, because on the test lot the lipopeptides-producing bacteria and cellulases-producing bacteria enhanced the digestibility of roughages in digestive tracts.

Application 11: Example of Enhancing Feed Efficiency (A Case of Feed Additive and Compost from Feces and Urine Used to Crop)

| Objects | Fattening Swines (Landrace)<br>Onion (Sendai Yellow) |
|---|---|
| Test Term | September–June in the next year<br>Seedlings of onions were planted the end of October,<br>harvested the middle of June.<br>(in Miyagi Prefecture) |

| Litters: | |
|---|---|
| Test Lot | Shavings |
| Control Lot | Straws |
| Bacterial Preparation: | |
| Test Lot | the same as in Application 8 |

Use of Preparation:

The preparation was mixed well with the formula feed for fattening swines at the ratio of 0.1% before feeding. The swines whose average weight were 60 kg were fed for 2 month on both of the lots for sales. The feces of swines including shavings on the test lot were collected 1 month after the beginning of the test. Then 2 t/10a of the compost were blended into soil, and covered with soil 10–15 cm deep. Seedlings of onions was planted 4 days after that. The feces of swines on the control lot were piled and sometimes agitated for 2 months on the concrete floor. Then 3 t/10a of the compost was blended into soil.

Summary of Results:

Bad odors on the test lot almost disappeared nearly 2 weeks after the beginning of blending in September. The content of ammonia in the barns after 1 month: 4ppm.

| Average Weight Gains per Day per Head | |
|---|---|
| (The values were measured in nearly 2 months.) | |
| test lot | 739 |
| control lot | 702 (g) |
| Yields of Marketable Onions: | |
| test lot | 5.88 |
| control lot | 5.27 (t/10a) |
| Average Weight of Onion: | |
| test lot | 395 |
| control lot | 345 (g) |
| Feed Efficiency: | |
| test lot | 25.7 |
| control lot | 24.4 (%) |

Description:

Though 3 t/10a of the compost was blended on the control lot, the yield of the onions on the test lot exceeded that of the onions on the control lot by 14%. The bulbs of the onions on the test lot were solid and compact and hard to germinate in storage. It is because the compost on the test lot, though it had not been fermented, not just causes no injuries to the roots of the onions but enhanced soil condition and affected favorably the growth of the onions.

Analysis:

Feed efficiency on the test lot exceeded that on the control lot by 5.3%. It was because digestion was enhanced by the lipopeptides-producing bacteria and cellulases-producing bacteria which propagated vigorously in the gut of the swines, and the physiological stress of the swines decreased with deodorization of the bad odors in the barns.

[The Effects of the Invention]

At first, the effects of the preparation as soil conditioner is described hereunder.

As is observed in Application 2 and 5, the preparation promotes formation of aggregates. Once sufficient aggregates are formed, the components of fertilizers are absorbed to the surface of the aggregates much more easily (which results in the increase in CEC), because the surface area of clay granules in soil is expanded drastically. Consequently, elevation of the components of fertilizers decreases, and thus the utility and maintainability of fertilizers increase. At the same time, the ability of plants to absorb fertilizers is enhanced and the growth of plant is promoted. Even when the preparation is employed to the field for the first time, the effect may be compared with that of continuous use of fully fermented composts over a long period. With the preparation, the average farmer can easily attain the effect of the highly-developing aggregates which can attain only by called exemplary farmers will bring about in a short time, labor-savingly, and economically.

As is observed in Application 1–5 and 7, the preparation spares the trouble and time to compost cellulosic materials. Instead of piling cellulosic materials in special facilities until they are fully fermented, blend them into soil just before the planting of seedlings or sawing of seeds; no injuries to the growth of crops are observed. The preparation is labor-saving and economical.

Besides, the preparation can prevent the injuries to the roots of crops caused by nematodes, because nematodes tend to avoid organic acids such as formic acid, acetic acid, lactic acid, which are secreted by the bacteria of the preparation in the process of degrading cellulosic materials in cultivated soil. Also from this point of view, the preparation is useful to prevent the injuries caused by continuous cropping.

If farmers continuously use the preparation with cellulosic materials for 2–3 years, minutely degraded cellulosic materials or humus become abundant 30–40 cm under the ground, where aggregates form easily. Consequently, the roots of crops are hard to be dried up even when atmospheric drying continues for a long time, because water may be supplied through the pore-spaces between aggregates from water veins deep under the ground by capillary action, and the water is maintained in the aggregates. It also means that the bacterial group can propagate more stably in the microspaces. Still, crops are hard to be flooded when it heavily rains, because around the aggregates water permeability is high and water is easily drained into the ground. The preparation provides good conditions for the growth of crops.

Furthermore, the roots of crops can vigorously elongate horizontally and vertically, and ryzosphere is expanded (especially roots hair developed), because around the aggregates water permeability is high and the amount of the components of fertilizers which cannot be absorbed to the aggregates decreases (which results in the decrease in EC). Consequently, nutrients are more easily absorbed through roots in soil, and therefore crops grow vigorously, stems and leaves develop vigorously, photosynthesis was activated and the yield and quality of the products become higher.

As is observed in Application 7, in cultivation of perennial or permanent crops over a long period, farmers can attain the sufficient effects of the preparation by at most one dosage per year, especially when the nitrogen-fixing bacteria are co-used. It is because the life of bacteria of the preparation is much longer. More specifically, when slowly degraded cellulosic materials (such as twigs, shavings, and timber tips) are put into cultivated soil together with rapidly degraded cellulosic materials (such as straws, fallen leaves and green stems and leaves after harvest), groups of bacteria propagate consuming the latter as nutrients in the early stage of crop cultivation, and then consuming the former. The degradation of the cellulosic martials is promoted both by lipopeptides which is secreted over a long period, and by cellulases which is secreted with lipopeptides. Hence, with LP nitrogen fertilizers which maintain the effect over a long period, the frequency of blending cellulosic materials and the preparation reduces.

Thus, in cultivation of perennial or permanent crops such as devil's tongue (*Amorphophallus konjac*), Japaneseudo (*Aralia cordata*), asparagus, fruit trees in general, tea, mulberry trees, perennial flowers and ornamental plants, farmers can gain tremendous effects with the preparation, even when marketed preparations can scarcely be expected to attain sufficient effects.

As is observed in Application 1, 4, 5, and 7, the preparation efficiently attains the effects in spring even when it is blended in late autumn or early winter of the last year and passes winter, because the life of the bacteria of the preparation is much longer, and it comprises spore-forming bacteria which are highly stable. Since the preparation, unlike marketed ones, may be employed in slack seasons for farmers and attain sufficient effects, it is also useful from the viewpoint of labor distribution.

Moreover, in the temperate region there are many crops which are cultivated over winter in open fields: wheat, cabbage, onion, burdock (*Arctium lappa*), barley, Chinese cabbage, horse radish, spinach, lettuce, long onion, potato, carrot, garlic, pea, etc. As is observed in Application, which describe applications of cultivation of the first four crops, when farmers employ the preparation to these crops before winter, the effect may be attained sufficiently from early spring to harvest time.

The preparation can attain higher effects if aggregates in soil are formed more easily. However, in cultivation of crops which are cultivated on sandy soil such as burdocks (as is observed in Application in 4) and Chinese yam (*Dios-corea batatas*), or crops which are cultivated on red colored soil in the sub-tropical or tropical region such as pineapple and sugar cane, micro-spaces, where microbs can propagate, are hard to be formed, because there are less clayey soil or humus. In order to attain sufficient effects, therefore, it is necessary to blend slowly-fermented cellulosic materials after the processing of propagating the bacteria in microspaces comprising porous silicic powders.

Garbage, by-products from foods or food processing materials, is hard to be disposed near residence areas because usually bad odors are produced in the fermentative process. However, the preparation prevents most of the bad odors, and as is observed in Application 3, composts processed by the preparation produce no injurious substances to the roots of crops, even though they are insufficiently fermented. When local governments collect garbage from home and dispose it, they can do so near residence areas without producing bad odors if the preparation are properly used. Also, when farmers compost cellulosic materials, they can do so in a short time without aeration or mixing in the piling process. Since there is no need of building special facilities processing garbage or compost, it is economical as well as labor-saving.

In composting cellulosic martials which are hard to be fermented such as bark, it is usually necessary to pile more than 2 years until the compost is fully fermented so that no injurious substances are produced. If marketed microbial preparations are employed to enhance composting, it is necessary to pile more than half a year as well as to aerate and agitate from time to time. However, As is observed in Application 6, if the compost was properly processed by the preparation, it will be applicable in less than 3–4 months, producing no injurious substances. Considering injuries to the roots by marketed composts of bark which are unfermented are often observed, especially in cultivation in green houses, it is advantageous.

In plant cultivation in recent years, farmers often employ organic fertilizers only (or at least mainly). As a matter of fact, organic fertilizers, like compost, should be piled for a certain period and degraded to a considerable degree before blending them into soil, because if unfermented organic materials are immediately blended into cultivated soil, volatile nitrogen substances are produced which are injurious to roots and decrease productivity. As is observed in Application 4, however, when the preparation are employed with organic fertilizers, no injuries to the roots are observed even when almost no time is taken for piling, because volatile nitrogen substances are not produced.

Also, while other anaerobic microbial preparations become unstable in contact with air, the preparation is stable in contact with air and in the presence of other substances because the preparation comprises spore-forming bacteria. Therefore, even if the preparation is mixed with organic fertilizers before sprinkling, the effects do not change. The product comprising dried organic fertilizers mixed with the preparation is marketable and would save a lot of labor. It is also possible to dissolve the preparation into water before sprinkling.

Secondly, the effects of the preparation in animal husbandry is described hereunder.

As is observed in Application 8 and 9, the preparation is useful as low-cost deodorizing material because it prevents bad odors from animal barns, which annoy residents nearby. Also, as is observed in Application 8, if the preparation are employed in cattle barns, no flies are observed, because no volatile bad odor substances such as ammonia are produced.

Also, mixtures of litters and feces from animal barns, which are hard to be dumped or disposed, are utilized as compost if they are properly processed by the preparation. So far, when farmers try them as compost, they have caused some injuries to the growth of crops, because they usually contain unfermented cellulosic materials such as shavings and timber tips which produce substances injurious to the roots of crops such as phenols and volatile nitrogen substances. Of course, if they are piled for 5–6 months even in warm seasons so that shavings and timber tips are fully degraded, it may be utilized, but it is too troublesome to be practiced. On the other hand, with the preparation, as is observed in Application 9, it is possible to blend them into soil without piling, because they not only produce no injurious substances but also suppress the propagation of groups of bacteria producing these substances. Considering in plant cultivation it is difficult to obtain compost of high quality, the preparation is very useful.

Still, when the adequate amount of the present preparation is blended into drainage of animals barns, as is observed in Application 8, they are no longer injurious to the growth of plants even though they are sprayed over crop cultivated fields soon after they are collected from barns. It is because lipopeptides and cellulases are secreted in the drainage, which speedily degrade straws and other cellulosic materials in it. Also the flowability of the drainage increase and it is easy to be disposed.

The preparation is useful even if it is sprinkled over animal barns from late autumn to early spring, because, as is observed in Application 8, the preparation comprising spore-forming bacteria which are very stable can pass the winter and attain the effects in early spring, when the problems of bad odors and disposing drainage are beginning to assume massive proportions.

As well, because the preparation sprinkled over animal barns prevent bad odors, the physiological stress of animals decrease. As is observed in Application 8, the production of milk of dairy cattle increases; as is observed in Application 9, the egg laying rate of layers increases.

Last of all, the effects of the preparation as feed efficiency enhancer is described hereunder.

As is observed in Application 10, in employing the preparation as feed efficiency enhancer, the effects are most remarkable when it is blended into roughage which is abundant in cellulosic materials. In addition, bad odors excreted from the feces of animals are prevented by blending. As is observed in Application 11, the effects are observed when it is blended into formula feeds. Also, as the result of decrease in undigestible feeds, stickiness of feces decrease. It is useful from the viewpoint of disposing feces and urines.

While the present invention has been described in terms of a battery support and replacement system, one skilled in the art will realize that the structure and techniques of the present invention can be applied to many appliances. The present invention may be applied in any situation where system components are sought to be rapidly and easily replaced with due consideration to insuring that proper polarity is maintained.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A bacterial preparation useful for soil conditioning comprising, in combination a soil-conditioning effective amount of a biologically pure culture of:

lipopeptide-producing bacterial strains selected from the group consisting of *Bacillus subtilis* producing the identifying lipopeptide of ATCC 21332, and *Bacillus lichenformis* producing the identifying lipopeptide of ATCC 39307; and cellulase-producing bacterial strains selected from the group consisting of *Bacillus subtilis* producing the identifying cellulase of ATCC 6051, *B. lichenformis* producing the identifying cellulase of ATCC 14580, *B. circulans* producing the identifying cellulase of ATCC 9500, *B. polymyxa* producing the identifying cellulase of ATCC 842, *Clostridium cellulolyticum* producing the identifying cellulase of ATCC 35319, and *Cl. aerotolerans* producing the identifying cellulase of ATCC 43524;

and wherein each bacterial strain is present in a carrier in a soil conditioning effective concentration.

2. The bacterial preparation of claim 1 and wherein each bacterial strain is present in a carrier in a concentration range of from about $10^4$ to about $10^9$ cells per gram.

3. A process for conditioning soil comprising the steps of:
preparing an amount of from about 5 to about 20 kg of a preparation of a soil-conditioning effective amount of a biologically pure culture of:

(1) lipopeptide-producing bacterial strains selected from the group consisting of *Bacilus subtilis* producing the identifying lipopeptide of ATCC 21332, and *Bacillus lichenformis* producing the identifying lipopeptide of ATCC 39307; and (2) cellulase-producing bacterial strains selected from the group consisting of *Bacillus subtilis* producing the identifying cellulase of ATCC 6051, *B. lichenformis* producing the identifying cellulase of ATCC 14580, *B. circulans* producing the identifying cellulase of ATCC 9500, *B. polymyxa* producing the identifying cellulase of ATCC 842, *Clostridium cellulolyticum* producing the identifying cellulase of ATCC 35319, and *Cl. aerotolerans* producing the identifying cellulase of ATCC 43524;

and a carrier and wherein each bacterial strain is present in said carrier in a concentration range of from about $10^4$ about $10^9$ cells per gram; and spreading said preparation over a surface area of about 10a.

* * * * *